US 9,718,154 B2

(12) United States Patent
Guo et al.

(10) Patent No.: US 9,718,154 B2
(45) Date of Patent: Aug. 1, 2017

(54) SLOT MACHINING

(75) Inventors: Changsheng Guo, South Windsor, CT (US); Trevor S. Smith, East Hampton, CT (US)

(73) Assignee: United Technologies Corporation, Farmington, CT (US)

( * ) Notice: Subject to any disclaimer, the term of this patent is extended or adjusted under 35 U.S.C. 154(b) by 572 days.

(21) Appl. No.: 13/352,764

(22) Filed: Jan. 18, 2012

(65) Prior Publication Data
US 2013/0183888 A1 Jul. 18, 2013

(51) Int. Cl.
| | | |
|---|---|---|
| B23P 15/00 | (2006.01) |
| B24B 19/02 | (2006.01) |
| B23C 3/30 | (2006.01) |
| B24B 19/14 | (2006.01) |
| G01N 3/58 | (2006.01) |

(52) U.S. Cl.
CPC .............. *B23P 15/006* (2013.01); *B23C 3/30* (2013.01); *B24B 19/02* (2013.01); *B24B 19/14* (2013.01); *G01N 3/58* (2013.01); *B23C 2220/04* (2013.01); *B23C 2220/366* (2013.01); *B23C 2220/48* (2013.01); *G05B 2219/45147* (2013.01); *Y10T 29/49996* (2015.01)

(58) Field of Classification Search
CPC . B23D 1/08; B23D 1/20; B23D 37/04; B23D 37/10; B23P 15/04; B23P 15/006; G06F 19/00; G06F 17/5018; G05B 19/4097; G05B 2219/45147; B23C 3/30; B24B 19/02; B24B 19/14; G01N 3/58
USPC ............... 451/57; 29/558; 700/173–175, 182
See application file for complete search history.

(56) References Cited

U.S. PATENT DOCUMENTS

| | | | | | |
|---|---|---|---|---|---|
| 1,614,558 | A | * | 1/1927 | Kasley ........................ | 409/131 |
| 4,707,793 | A | * | 11/1987 | Anderson .................... | 700/188 |
| 4,833,617 | A | * | 5/1989 | Wang .......................... | 700/173 |
| 5,377,116 | A | * | 12/1994 | Wayne et al. ............... | 700/175 |
| 5,430,936 | A | * | 7/1995 | Yazdzik et al. ............. | 29/889.2 |
| 5,689,062 | A | * | 11/1997 | Jawahir et al. ............. | 73/104 |
| 5,691,909 | A | | 11/1997 | Frey et al. | |

(Continued)

FOREIGN PATENT DOCUMENTS

WO 2005/036287 A2 4/2005

OTHER PUBLICATIONS

Li et al, Framework of Grinding Process Modeling and Simulation Based on Microscopic Interaction Analysis, 2011 (presented 2009), Robotics and Computer-Integrated Manufacturing, vol. 27, issue 2, pp. 471-488.*

(Continued)

*Primary Examiner* — Monica Carter
*Assistant Examiner* — Marcel Dion
(74) *Attorney, Agent, or Firm* — Bachman & LaPointe, P.C.

(57) ABSTRACT

A method for cutting a blade root retention slot in a turbine engine disk element includes forming a precursor slot in the element. The precursor slot has first and second sidewalls and a base. A rotating bit is passed through the precursor slot to machine the base. The bit rotates about an axis off-normal to a direction of passing. A cutting performance of the rotating bit is modeled reflecting a chip trapping intensity parameter and a heat intensity parameter. At least one parameter of the bit and its passing is selected so as to avoid tool loading where removed chips/swarf stick onto the bit.

21 Claims, 9 Drawing Sheets

(56) References Cited

U.S. PATENT DOCUMENTS

| | | | |
|---|---|---|---|
| 5,801,963 A | | 9/1998 | Sadler et al. |
| 6,449,529 B1 | | 9/2002 | Oleksy |
| 7,007,382 B2 | * | 3/2006 | Mantel ........................ 29/889.2 |
| 7,530,882 B2 | * | 5/2009 | Soma et al. .................... 451/11 |
| 7,751,917 B2 | * | 7/2010 | Rees et al. ...................... 700/97 |
| 7,933,679 B1 | * | 4/2011 | Kulkarni et al. ............. 700/173 |
| 8,567,059 B2 | * | 10/2013 | Jette et al. ................... 29/889.2 |
| 2004/0064944 A1 | * | 4/2004 | Packman et al. ............ 29/889.2 |
| 2005/0015983 A1 | | 1/2005 | Mantel |
| 2006/0212159 A1 | * | 9/2006 | Battistella et al. ........... 700/175 |
| 2009/0220312 A1 | * | 9/2009 | Shamoto et al. ............. 407/114 |
| 2009/0287458 A1 | * | 11/2009 | El-Wardany et al. ............ 703/1 |
| 2010/0114354 A1 | * | 5/2010 | Lee ............................... 700/103 |
| 2010/0325852 A1 | | 12/2010 | Frederick |
| 2011/0008172 A1 | * | 1/2011 | Jette ........................ B24B 19/02 |
| | | | 416/219 R |
| 2011/0014002 A1 | | 1/2011 | Storch et al. |

OTHER PUBLICATIONS

International Search Report and Written Opinion for PCT/US2013/020624, dated Mar. 1, 2013.
European Search Report for EP Patent Application No. 13738146.3, dated Sep. 9, 2015.

\* cited by examiner

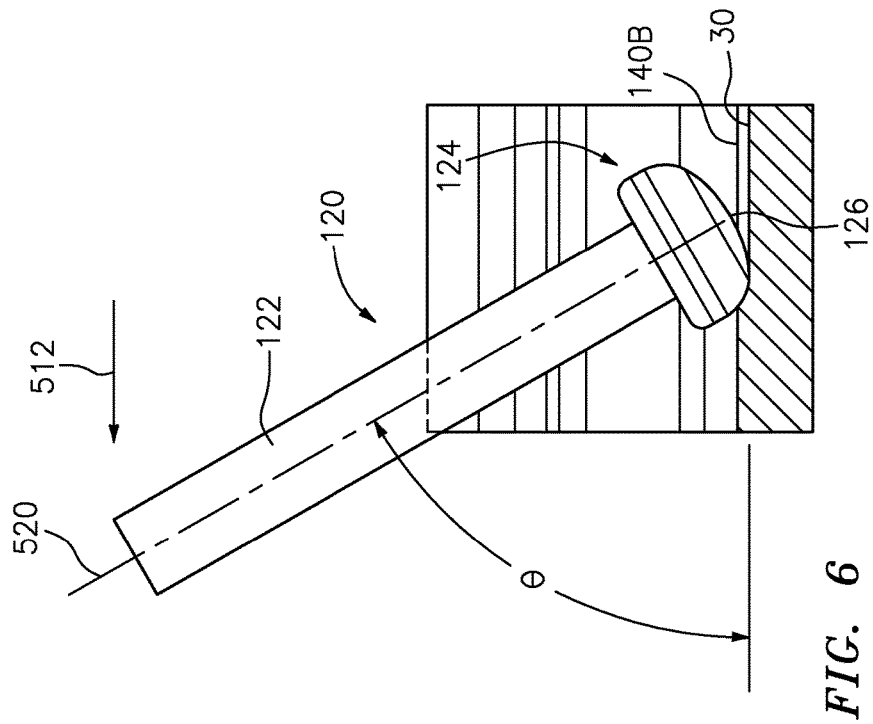
FIG. 6
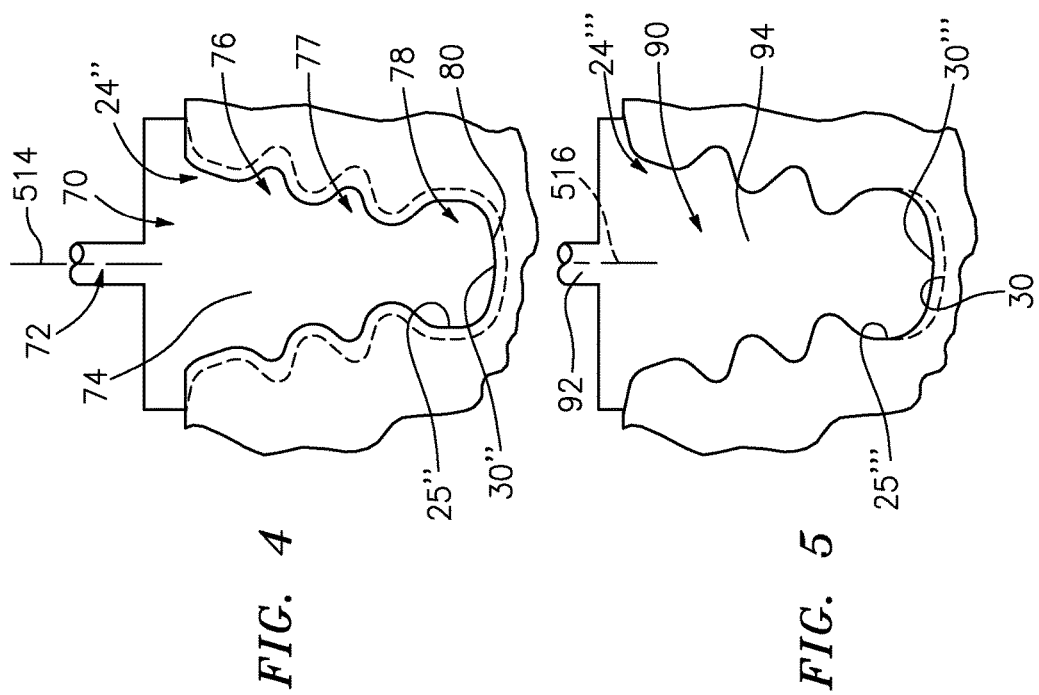
FIG. 4
FIG. 5

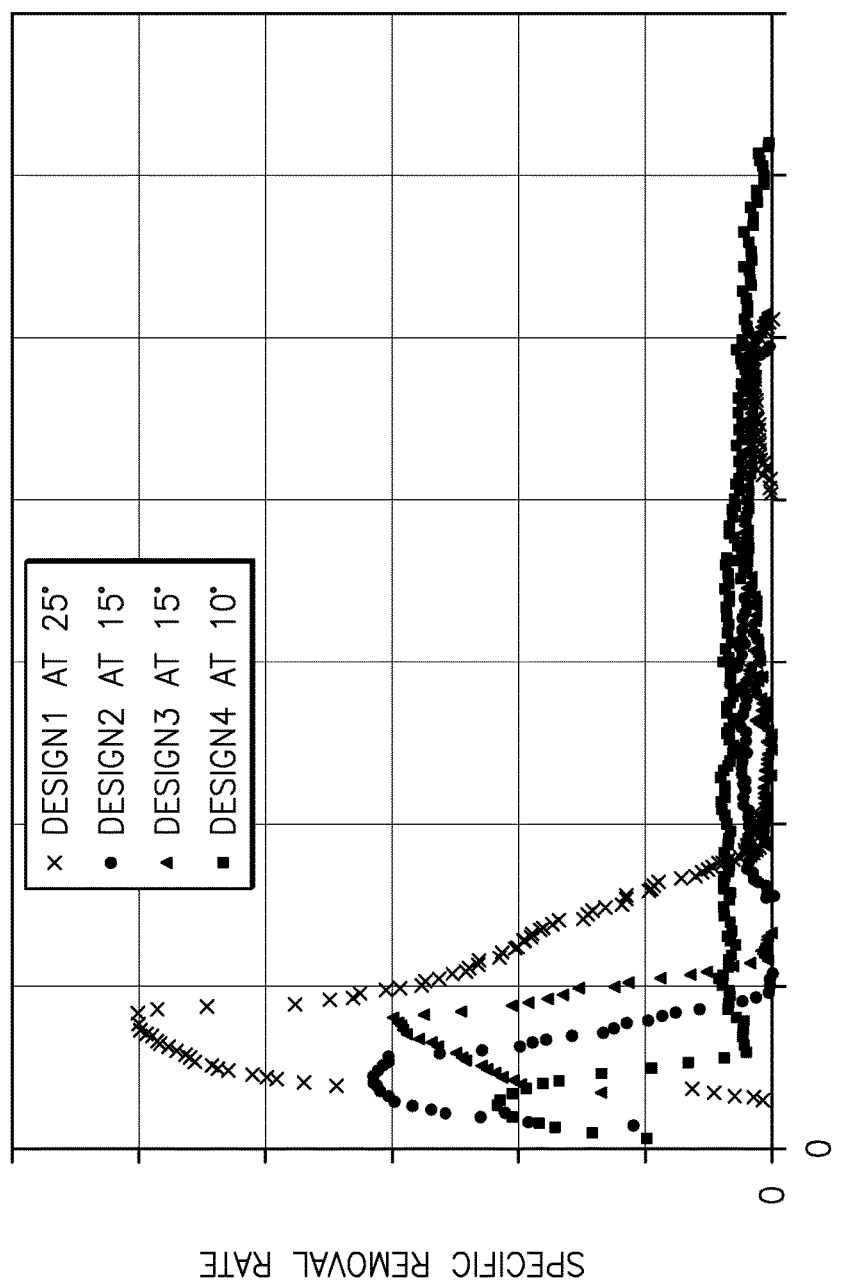

SLOT MACHINING

BACKGROUND

The disclosure relates to machining. More particularly, the disclosure relates to the machining of blade attachment slots in turbomachine disks.

In turbomachines such as gas turbine engines, the blades of fan, compressor, and turbine sections may be secured to separate disks. One attachment means involves providing blade roots having a convoluted section complementary to a convoluted section of slots in the disk periphery. An exemplary configuration involving a convoluted profile that generally increases in transverse dimension from the slot base toward its opening is called a fir tree configuration. A number of methods have been used or proposed for forming the slots. For a long time, the state of the art method for forming the slots involves a broaching process with hundreds of broach cutters in a linear assembly. After an initial machining of a slot precursor, the disk is translated along the broach which may be many tens of meters in length. Cutter profile progressively changes from that of the initial slot precursor to that of the final slot. Such broaching process requires a very substantial capital investment as well as substantial maintenance.

A recently-proposed alternative is found in U.S. Pat. No. 7,007,382 (the '382 patent). In the '382 patent, a small number of rotating abrasive bits are used to transform the precursor slot into the final slot shape. One example involves a first bit having a profile nearly that of the final slot over a depth extending to near the base of the final slot. A second stage involves a bit of essentially the final slot shape over such or slightly different depth. A final pass machines the base of the slot and involves passing a bit rotating about an axis off-normal to a direction of the passing. The off-normal rotation ensures that the bit is continuously moving relative to the disk metal it contacts.

SUMMARY

With reference to the exemplary machining of the '382 patent, the pass taken by the final bit may leave a surface mismatch at the boundary between the surface portion that it machined and the adjacent surface portion machined only by prior bits. The process and associated bits and/or the nominal slot profile may be configured to limit performance debits associated with the mismatch.

Accordingly, one aspect of the disclosure involves a method for cutting a blade root retention slot in a turbine engine disk element. A precursor slot is formed in the element. The precursor slot has first and second sidewalls and a base. Subsequent to the forming, a convoluted profile is machined into the first and second sidewalls. Subsequent to the machining, a rotating bit is passed through the precursor slot to machine the base, the bit rotating about an axis off-normal to a direction of the passing. The cutting performance of the rotating bit reflecting a chip trapping intensity parameter and a heat intensity parameter is modeled. At least one parameter of the bit (e.g., its geometry) and its passing (e.g., the relationship of its rotational axis to the direction of passing) may be selected so as to avoid tool loading where removed chips/swarf stick onto the bit.

In various implementations, the machining may broaden and deepen the base or, alternatively, the machining may leave at least a first portion of the base intact from the forming. The forming may involve machining with a grinding wheel rotating about a wheel axis essentially perpendicular to a direction of passing and essentially circumferential to a central longitudinal axis of the disk element. The machining may involve machining with a profiling bit having a convoluted longitudinal profile complementary to the convoluted profile of the slot sidewalls. The passing may smooth transitions between the first and second sidewalls and the base. During the passing, the bit axis may essentially lie along a radial plane of the disk element at an angle of between 60° and 85° relative to the direction of its passing. During its passing, the bit axis may be inclined relative to the direction of its passing. The forming may involve machining with a grinding wheel having portions of different diameters for forming the precursor slot with the first and second sidewalls as stepped sidewalls. The passing may increase an outward concavity of the base. Another aspect involves a turbine engine blade stage having a disk element with a circumferential array of convoluted profile attachment slots. Each slot has first and second sidewalls and a base. A circumferential array of blades have attachment roots received in respective said slots. The slots have a curvature mismatch proximate junctions of each sidewall and the base. The curvature of mismatch is remote of a high operational stress location along the slot.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 4 is a view of a secondary precursor of the disk of FIG. 1.

FIG. 5 is a view of a tertiary precursor of the disk of FIG. 1.

FIG. 6 is a radial cutaway view of the disk of FIG. 1 during machining from the precursor of FIG. 5.

FIG. 12 is a plot of specific removal rate against the discretized segments of four exemplary tools.

Like reference numbers and designations in the various drawings indicate like elements.

DETAILED DESCRIPTION

Figure 1:
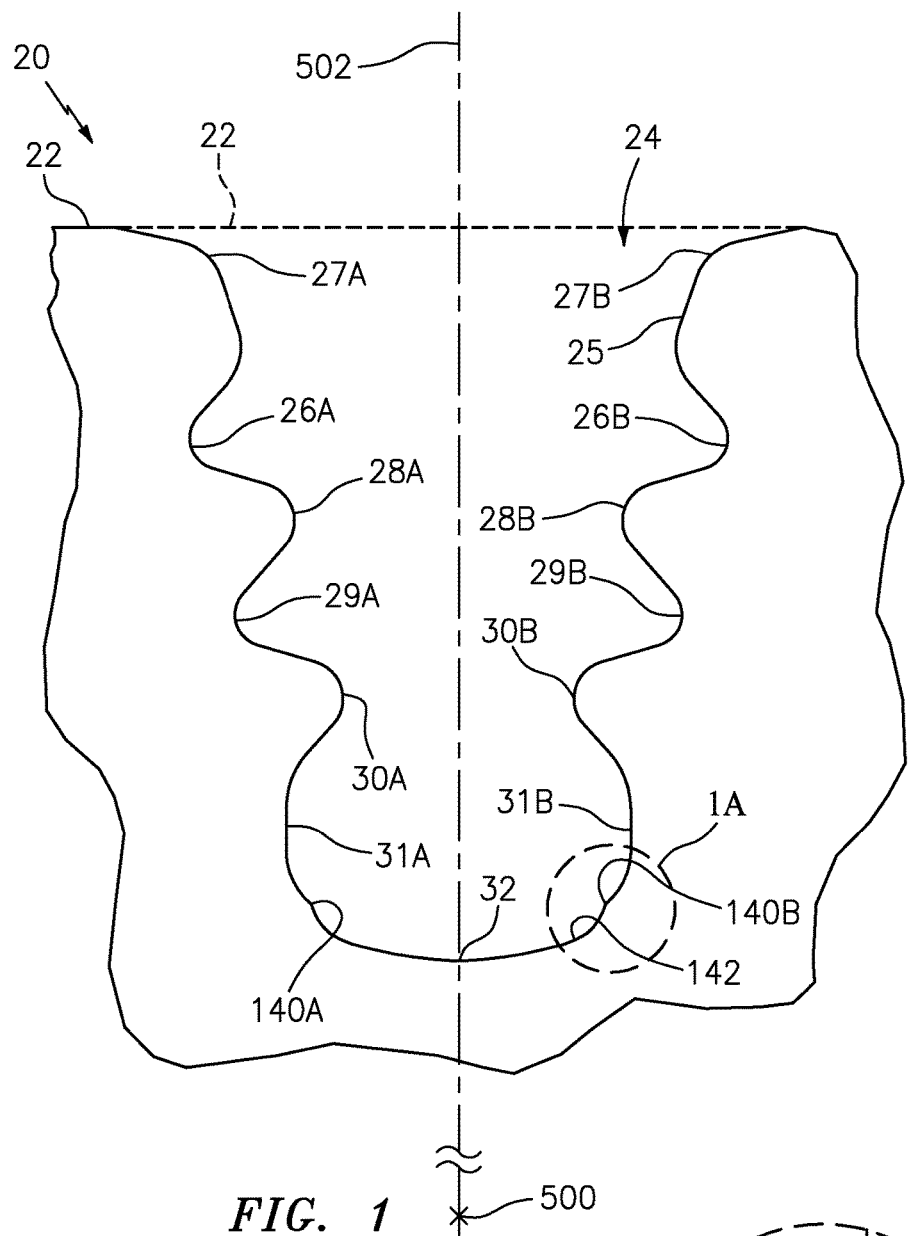
FIG. 1 is a partial longitudinal view of a blade slot attachment in a disk.
Figure 1A:
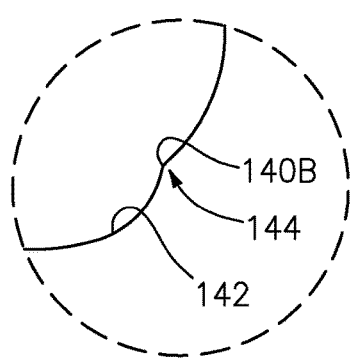
FIG. 1A is an enlarged view of a mismatch region of the slot of FIG. 1.

FIG. 1 shows a disk 20 having a central longitudinal axis 500 and a circumferential perimeter 22. Extending radially inward from the perimeter are a circumferential array of firtree blade attachment slots 24 each defined by a surface 25 forming the sidewalls and base of the slot. In the exemplary embodiment, each slot 24 extends along a symmetry plane 502 which may be a longitudinal radial plane through the axis 500 or may be at an angle to the axis 500. Each slot 24 has a convoluted profile for receiving a complementary root or button of a blade (not shown) to secure the blade to the disk against centrifugal forces associated with rotation of the disk about its axis 500. The exemplary slot has three relatively wide portions respectively radially inward of associated relatively narrow portions. In the exemplary embodiment, an outboard wide portion is defined between sidewall portions 26A and 26B of the surface 25 on either side of the plane 502. Radially outboard thereof the associated relatively narrow portion is formed between sidewall surface portions 27A and 27B. Radially inboard thereof is a relatively narrow portion defined by sidewall surface portions 28A and 28B. Yet further inboard, the second relatively wide portion (although not as wide as the first) is defined by sidewall surface portions 29A and 29B followed by a second relatively narrow portion defined by surface portions 30A and 30B, a third relatively wide portion defined by surfaces 31A and 31B and finally a base 32 extending therebetween in a smooth continuously curving fashion.

Figure 2:
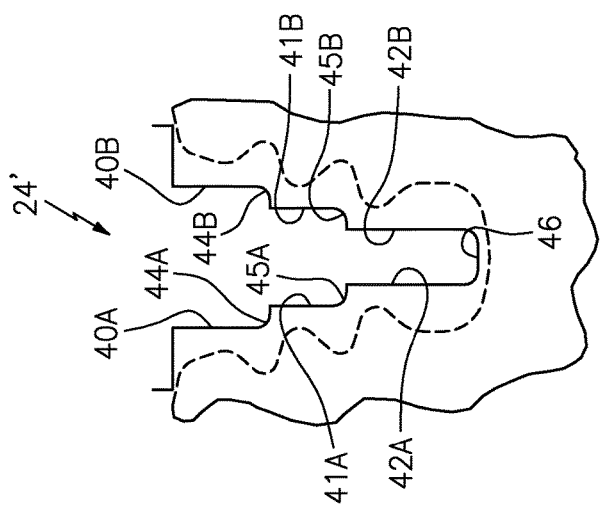
FIG. 2 is a view of a first precursor of the disk of FIG. 1.
Figure 3:
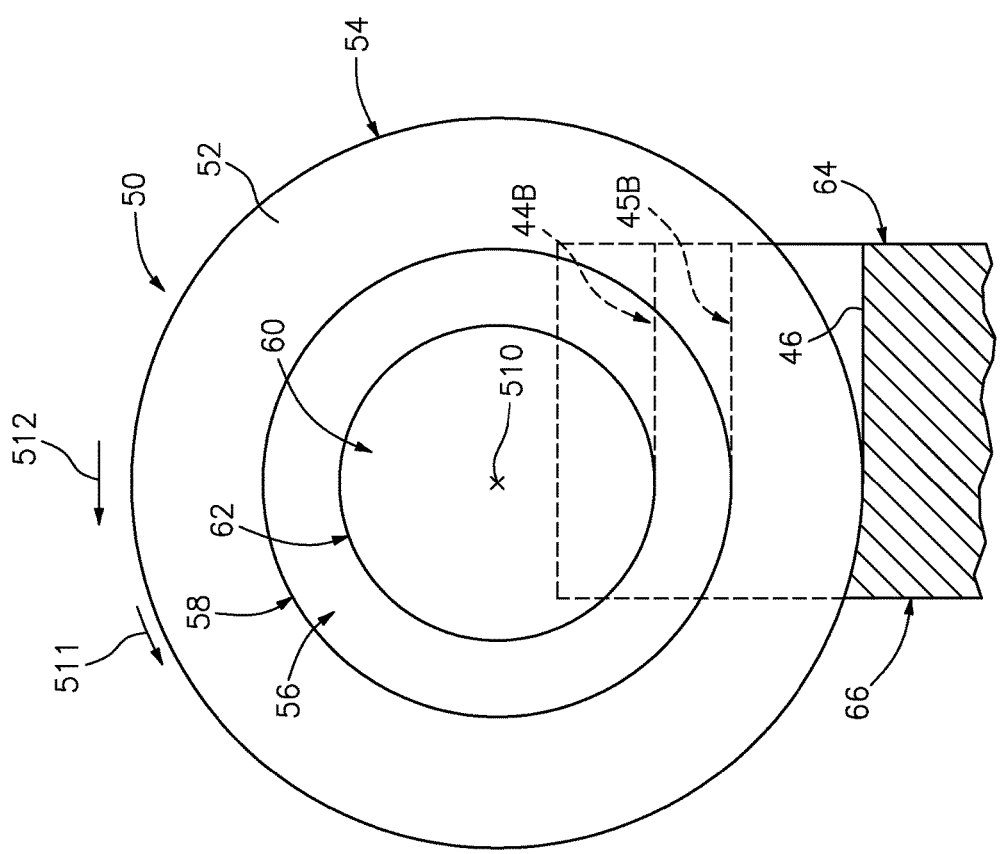
FIG. 3 is a radial cutaway view of the precursor of FIG. 2 during machining.

In an exemplary method of manufacture, a precursor of the final disk is initially formed with a substantially uninterrupted perimeter. Initial precursor slots 24' (FIG. 2) may be ground having an outboard portion between relatively widely spaced parallel sidewall surface portions 40A and 40B—an intermediate portion between more closely spaced surface portions 41A and 41B, and an inboard portion with yet more closely spaced surface portions 42A and 42B. Respective essentially circumferential sidewall shoulder surface portions 44A, 44B; 45A, 45B separate these surface portions. A flat base surface 46 joins the surface portions 42A and 42B. FIG. 3 shows the initial slot precursor being ground by a grinding wheel 50 having a large diameter central portion 52 having a perimeter 54 for forming the base surface 46 and first and second sides for forming the surface portions 42A and 42B. The grinding wheel has a pair of intermediate diameter portions 56 each having a perimeter 58 for forming an associated one of the surface portions 45A, 45B and an outboard side surface for forming an associated one of the surface portions 41A, 41B. The grinding wheel has a pair of smaller diameter portions 60 each having a perimeter 62 for forming an associated one of the surface portions 44A, 44B and an outboard side surface for forming the associated surface portion 40A, 40B. The wheel is driven for rotation about its central axis 510 in a direction 511 while being traversed in a longitudinal direction 512 to pass the wheel between first and second sides 64 and 66 of the disk. Instead of using a stepped wheel with different diameters (e.g., three as described here), the roughing of the slot may be done using sequential non-stepped wheels (e.g., three). This allows use of wheels of simpler geometry and lower cost.

A convoluted secondary slot precursor 24" (FIG. 4) is then formed from each initial precursor 24'. In the exemplary embodiment, this is done using a superabrasive bit 70 driven for rotation about its central longitudinal axis 514 while being traversed in the direction 512. The exemplary bit has a shaft 72 for mounting in an associated machine tool (grinding and/or milling machine) (not shown) and a distal superabrasive coated tip 74. The tip is dimensioned with proximal, intermediate, and distal relatively wide portions 76, 77, and 78 for forming associated portions of a surface 25" of the secondary slot precursor 24". The surface 25" is slightly toward the plane 502 relative to the ultimate surface 25. In the exemplary embodiment, the tip 74 includes a distal end 80 for forming a base portion 30" on surface 25" similarly slightly outboard of the ultimate base.

Each slot precursor 24" is, in turn, further enlarged to form a third precursor 24''' (FIG. 5). This is done using a second bit 90 having a shaft 92 and tip 94 and rotated about its axis 516 while being traversed in the direction 512 as was the bit 70. Relative to the tip 74 of the bit 70, the tip 94 has corresponding portions of slightly greater diameter and is slightly longer. The exemplary bit dimensions bring the surface 25''' into alignment with the ultimate surface 25 except at a base 30''' slightly outboard of the ultimate concave base 30. At least one additional machining stage is provided to form the surface portion 30 with its outwardly concave shape. This is achieved by means of a bit 120 having a shaft 122 and a superabrasive tip 124 and being rotated about its axis 520 while being traversed in the direction 512. Because the rotation produces zero movement at the center 126 of the distal end of the tip 124, the axis 520 is off-radial. FIG. 6 shows the axis at a non-right angle $\theta$ to the longitudinal direction or feed direction 512 and thus off-radial by the component of $\theta$. With reference to the illustration of FIG. 6, the bit 120 is defined as inclined relative to the feed direction 512 for values of $\theta$ greater than zero and less than 90°. A decline is defined as $\theta$ values greater than 90° and less than 180°. In the exemplary embodiments, the axis 520 is off-radial by between 5° and 50° (40°≤$\theta$≤85°, more narrowly, between 10° and 30° (60°≤$\theta$≤80°).

FIG. 1 shows a boundary 140A, 140B on either side of the slot between a surface portion 142 machined by the final bit 120 and the surface portion outboard thereof machined only by prior bits. The exemplary boundary defines a protrusion 144. The boundary represents a concavity mismatch between the surface portion 142 and the surface portion outboard thereof.

To satisfy this requirement, machining both the bottom and the adjacent areas in one machining pass with tilt tools (120 of FIG. 6) is appropriate.

For some turbine disk slot designs, there are a number of possible tool designs to produce the slot. However, most of the tool designs will not be advantageous for production because the tool will fail unexpectedly under various machining conditions (speed, feed, and depth of cut, grit size etc). The nature of the tool premature failure seems always associated with a phenomenon called "tool loading" where the removed grinding swarf or chips stick back to the tool surface and significantly reduce the cutting capability of the tools. This has been verified experimentally.

It is time and cost prohibitive to design and procure various tools, experimentally evaluating their performances by conducting cutting experiments, and choosing the right tool designs that will work satisfactorily.

Thus, a new tool design method is provided for designing tools for machining the bottom and its adjacent areas of turbine disk slots with tilt-type tools (either abrasive tools such as plated CBN, brazed CBN, and vitrified CBN quills and/or milling cutters). The proposed method virtually evaluates the machining performance of the tools using model-based simulations. The method designs, evaluates, and selects the optimum tools.

Figure 7:
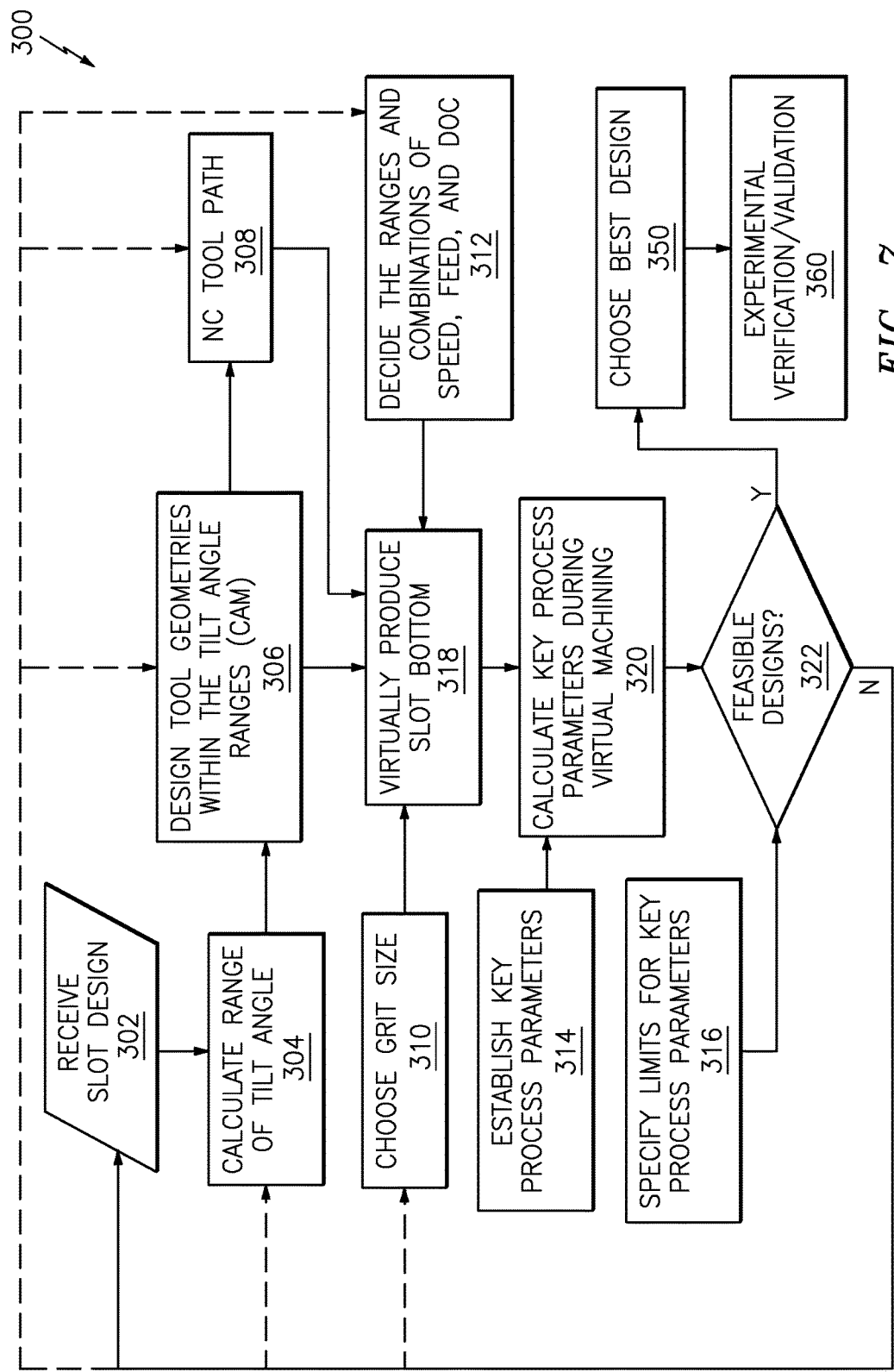
FIG. 7 is a flowchart of a tool design process.

FIG. 7 outlines the steps in the method 300.

The basic slot design (configuration) is received 302 (e.g., as a CAD file (solid model)). Based on the turbine disk slot geometry (length, width and depth) calculate 304 the length of the tilt tool required and decide the range of tilt angles to be used, for example 10-25 degrees. This is a geometric calculation done using Computer Aided Manufacturing (CAM) software. This assumes that the general combination of tools (e.g., one stepped grinding wheel followed by two profiled quills rotated at right angles to traversals followed by a final bottom milling quill at a tilt angle (e.g., as in the '382 patent)) is already decided.

Design 306 the tool geometries that can produce the required slot geometry within the tilt angle range chosen. This is done with CAM software. There is a range of geometries. Factors used by the CAM software are the tool workpiece contact length, the minimum surface speed near the tool tip.

The NC tool path may then be determined 308. The NC tool path may be a data file that the milling machine uses. The file specifies the position, speed, and feed that the tool will travel during machining. For example, one kind of NC tool path is known as "G-code". In one example, it may take five machining passes with each of the plated or vitrified CBN (e.g., wheels and bits) at a depth of cut of 0.002 inch (0.05 mm) per pass to finish the slot. In another example, it may take ten machining passes at a depth of cut of 0.001 inch (0.025 mm) per pass to finish the slot.

Separately choose 310 the grit size if abrasive machining is used, for example 170/220 grit. This is mainly based on the surface finish requirement considering the machining speed ranges which are determined by the tool diameter ranges and the spindle RPM.

Separately, decide 312 the range of possible machining parameters (speed, feed, and DOC) and possible combinations for evaluation. These are chosen by manufacturing engineers based on material and the tool. The tool geometry designed at step 306, the associated paths determined at 308, the grit size chosen at step 310, and the ranges decided at step 312 are then used by the system/method to virtually produce 318 (e.g., via a computer simulated virtual machining process) the slot bottom. This results in process parameters such as machining force, power, heat flux at the tool work contact zone, machining temperature, specific material removal rates, the chip trapping intensity parameter, and the heat intensity parameter (see below).

Separately, key process parameters are established 314. For example, specific material removal rate, chip trapping parameter and heat intensity parameter are among the key process parameters for superabrasive machining. These key process parameters are calculated by the model using the process setup parameters such as speed, feed, depth of cut, and the like. The equations for calculating the key process parameters are specified below. These equations are programmed in a language such as the C programming language and compiled as a dynamic link library (DLL) that runs under commercial software such as VERICUT software. For each machining step specified in the NC code, the DLL calculates the values of these parameters using the programmed equations. The calculated parameters are stored as a text file for use by step 322 (FIG. 7). One example is grit size 170/220, speed 60-90 m/s, and specific removal rate 3 mm^2/s. Another example will be grit size 100/120, speed 60-90 m/s, and specific removal rate 6 mm^2/s.

Separately the limits of key machining process parameters for successful machining are specified 316. The values of the limits depend on the material property and the tool being used. For example, the specific removal rate for a 170/220 grit plated CBN tool should not exceed 3 $mm^2/s$. It can be as high as 6 $mm^2/s$ for a 100/120 grit wheel. These limits establish the capability of the tool and the process. The process will most likely fail if these limits are violated. For example, the tool may fail quickly if the specific removal rate exceeds the established limit. These limits may be specified in tabulated format with grit size, wheel speed, and specific removal rate listed. The information is stored as a file for the virtual machining (machining model) to reference to during simulation (e.g., performed on the same computer). Some parameters are specified per lookup tables based on the tool type (e.g. grit size) and material (e.g. nickel-based superalloy, generally or a specific example such as alloy IN100). For example, the specific material removal rates are specified in this way. Some new parameters such as the chip trapping parameter and the heat intensity parameter are new. The model decides the limits. The common key parameters include specific removal rate, the tool-work contact length, the chip size, heat flux, and specific energy. As is discussed below, the exemplary embodiment also involves two additional parameters for the tilt tool machining. The first one is the chip trapping intensity parameter which is defined as the product of the specific removal rate and the contact length. The second one is called the heating intensity parameter (discussed below). The limits for the common and key parameters depend on the grit size if abrasive tools are used. For example, the specific removal rate for a 170/220 grit plated CBN tool should not exceed 3 $mm^2/s$.

Figure 8:
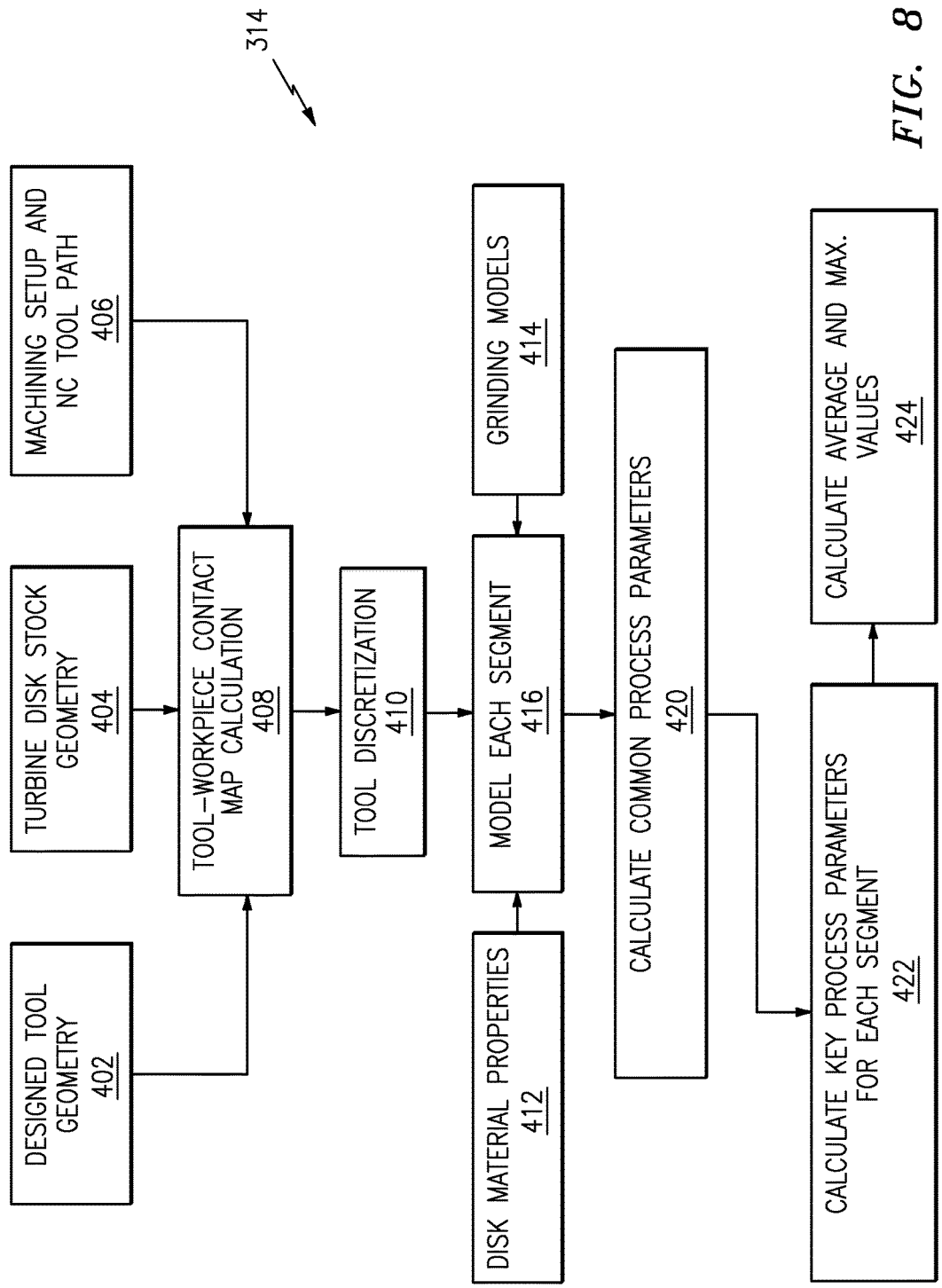
FIG. 8 is a flowchart of calculation of two parameters for the process of FIG. 7.

FIG. 8 (discussed below) outlines the steps for calculating 320 these two key parameters based upon the virtual slot bottom produced in step 318 and the parameters established at step 314.

This is a simulation that calculates all the common parameters and the two key parameters. The calculation includes the distribution of these parameters along the tool axis and the machining steps.

Figure 9:
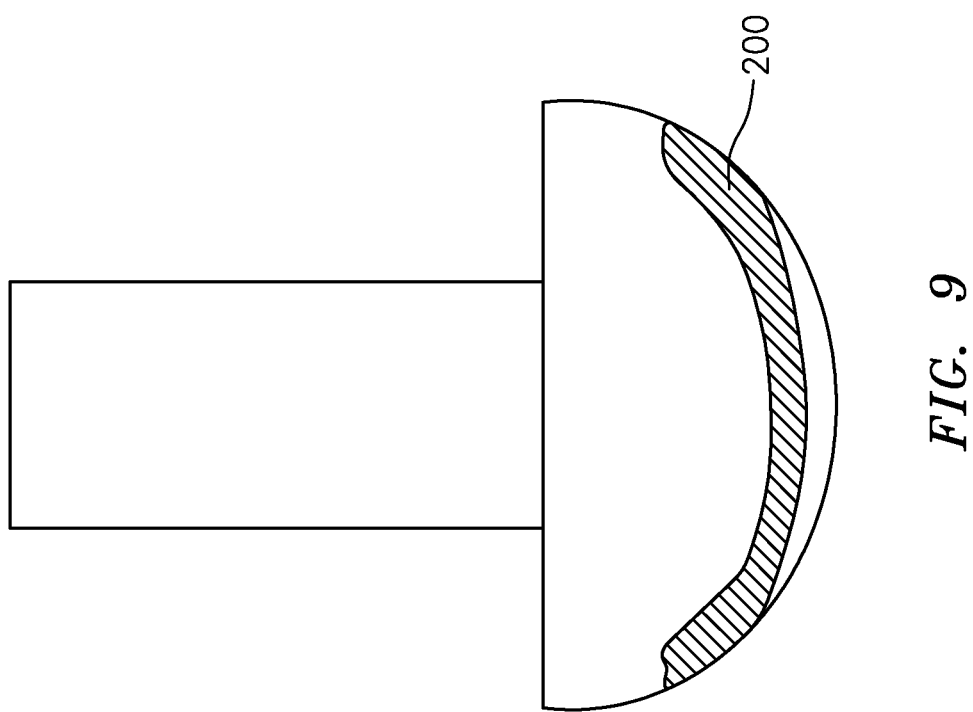
FIG. 9 is a tool-work contact map.

At cell 322, responsive to the limits established in step 316 and key process parameters calculated at block 320 and FIG. 8 it is determined whether any designs are feasible. For example, the process is considered feasible if all the key process parameters calculated are within the limits established. If any of the key process parameters calculated violates the associated limit, the process is considered infeasible. If no process designs are feasible, then the process repeats with the following: a new slot design at 302 and/or a revisit and revision of one or more of angle at 304, geometries at 306, and grit size at 310. The exemplary calculation starts with the tool workpiece contact map (as shown in FIG. 9) that contains information on the size and location of the tool workpiece contact during machining. The tool is then discretized into subtool segments. Grinding models (e.g., a force model that calculates grinding forces based on process parameters) are then applied for each discretized segment to calculate process parameters such as arc of contact, depth of cut, speed, feed material removal rate, and heat flux. Based on these typical process parameters, the key process parameters (chip trapping intensity parameter and heat intensity parameter) are also calculated for each segment. It is then determined whether any designs are feasible. This determination may be made by the software simulation.

If feasible designs have been produced, then the best (optimum) tool design is chosen among the feasible ones that satisfy the requirement of the key process parameter limits. The simulation chooses the best using the parameters outlined above.

The selected tool designs are experimentally verified and validated 360.

The unique key process parameters are described in further detail below.

Figure 10:
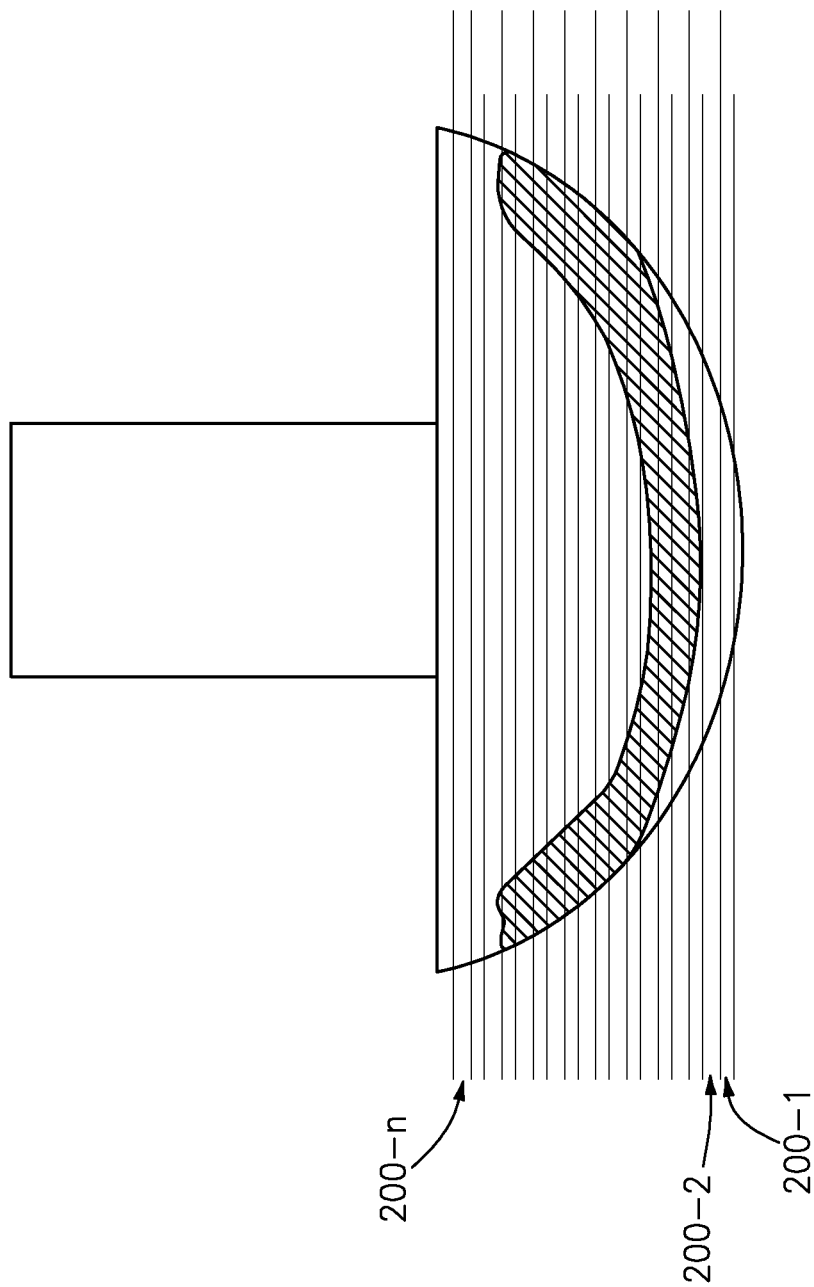
FIG. 10 is a discretized version of a contact map of FIG. 9.
Figure 11:
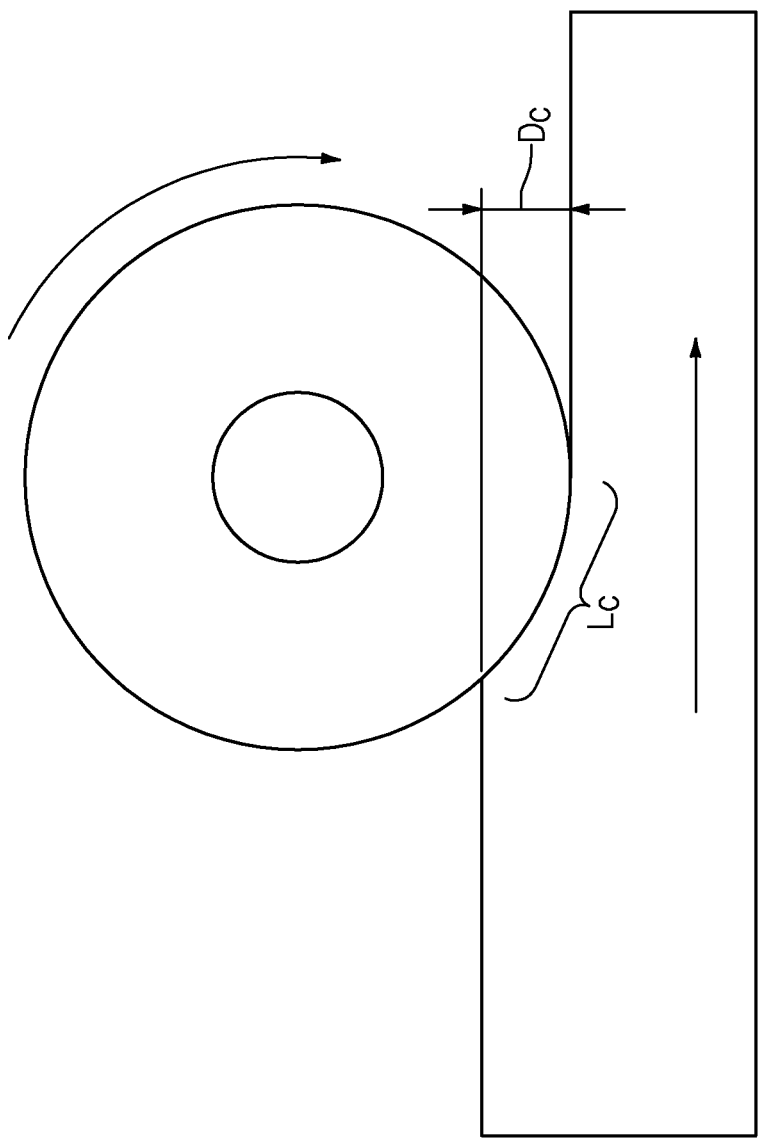
FIG. 11 is a schematic representation of cutting by one of the discretized segments of the map of FIG. 10.

When the tilt tool moves through the slot, the contact between the workpiece (slot) and the tool can be analyzed using the contact map (e.g., FIG. 9). As can be seen from this figure, the contact 200 situation between the tool and the workpiece varies axially along the tool. To fully understand this situation, it is appropriate to divide the tool into multiple segments 200-1 through 200-n (e.g., FIG. 10). Each segment of the tool can be analyzed using the simplified cutting disk model shown in FIG. 11. The material removal rate for each segment can be calculated as follows:

$$Z_w = D_C * \text{feed}$$

and the chip trapping intensity parameter is defined as:

$$cp = Z_w L_C$$

where $D_C$ is the depth of cut $L_C$ is the arc of contact length as shown in FIG. 11.

The heat intensity parameter is:

$$HI = \frac{Q}{k}\sqrt{\frac{\text{alpha} \cdot L_C}{\text{feed}}}$$

where Q is the heat flux at the tool-work contact zone, k is the thermal conductivity of the material, alpha is the thermal diffusivity of the material.

FIG. 8 shows the calculation 320. An initial calculation 408 calculates the tool-workpiece contact map (as shown in FIG. 9) 200. The contact map is the base for calculating all the process parameters in step 320, FIG. 7. The contact map contains information on the size and location of the tool-workpiece contact during machining. For example, the tool may only cut material with the tip or it may removal more material with the sides. This includes, as inputs, the designed tool geometry 402 (e.g., as a 3-D solid model), the turbine disk stock/precursor geometry 404 (e.g., as a 3-D solid model), and the machining setup and NC tool path 406 (e.g., as G-codes). The tool is then discretized 410 into the subtool segments. The resulting information along with disk material properties 412 and grinding models (e.g., a force model that calculates grinding forces based on process parameters) 414 for the particular abrasive are used as inputs for modeling 416 each discretized segment (e.g., as the grinding of an inclined surface). Typical process parameters are calculated 420 for each segment. Exemplary typical process parameters include arc of contact, depth of cut, speed, feed material removal rate, and heat flux. The key process parameters are also calculated 422 for each segment. The exemplary system involves calculating two key process parameters, namely, the chip trapping intensity and the heat intensity. Average and maximum values are then calculated 424 for these key process parameters.

The system may be implemented in a reengineering situation for a baseline slot and baseline manufacturing process. In one set of examples, the baseline process is generally similar and the reengineering involves shrinking and shifting the mismatch location. Alternatively, the baseline may not include a mismatch. For example, baseline manufacturing processes may involve long mandrels having a series of cutters of progressively varying profile. A baseline mandrel-formed slot may lack the mismatch described above. Minimizing the mismatch may allow replacement of the baseline mandrel process with a rotating bit manufacturing process, allowing use of the baseline blades in a similar performance envelope. In such a situation, the baseline slot may more closely accommodate the inboardmost lobe of the attachment root than does the modified version.

One or more embodiments have been described. Nevertheless, it will be understood that various modifications may be made. For example, in alternate embodiments, the intermediate radial quill machining may not necessarily disturb the base of the initial slot precursor. This base may end up being effected only by the angled quill. Furthermore, the principles may be applied to a number of existing basic disk configurations and manufacturing techniques. In such implementations, features of the implementation would be influenced by features of the disks and techniques. Accordingly, other embodiments are within the scope of the following claims.

What is claimed is:

1. A method for cutting a blade root retention slot in a turbine engine disk element, the method comprising:
   forming a precursor slot in the element, the precursor slot having first and second sidewalls and a base;
   subsequent to said forming, machining a convoluted profile into the first and second sidewalls; and
   subsequent to said machining, passing a rotating abrasive bit through the precursor slot to machine said base, the abrasive bit rotating about an axis off-normal to a direction of said passing,
   wherein the method further comprises:
   modeling a cutting performance of the rotating abrasive bit incorporating a chip trapping intensity parameter and a heat intensity parameter;
   calculating the heat intensity parameter as:

$$HI = \frac{Q}{k}\sqrt{\frac{\text{alpha} \cdot L_C}{\text{feed}}}$$

where Q is heat flux at the tool-work contact zone, k is thermal conductivity of material of the precursor, alpha is thermal diffusivity of the material of the precursor, and Lc is a contact length; and
   selecting at least one parameter of the abrasive bit and its passing so as to avoid tool loading where removed chips/swarf stick onto the bit.

2. The method of claim 1 wherein said machining broadens and deepens the base.

3. The method of claim 1 wherein the forming comprises machining with a grinding wheel rotating about a wheel axis essentially perpendicular to a direction of passing said grinding wheel and essentially circumferential to a central longitudinal axis of the disk element.

4. The method of claim 1 wherein the machining comprises machining with a profiling bit having a convoluted longitudinal profile complementary to said convoluted profile of said slot sidewalls.

5. The method of claim 1 wherein the passing smooths transitions between said first and second sidewalls and said base.

6. The method of claim 1 wherein during the passing, the bit axis essentially lies along a radial plane of the element at an angle of between 60° and 85° relative to said direction of said passing.

7. The method of claim 6 wherein the chip trapping intensity parameter is a product of a specific removal rate and a contact length.

8. The method of claim 1 wherein the forming comprises machining with a grinding wheel having portions of different diameters for forming the precursor slot with said first and second sidewalls as stepped sidewalls.

9. The method of claim 1 wherein the passing increases an outward concavity of the base.

10. The method of claim 1 wherein the chip trapping intensity parameter is a product of a specific removal rate and a contact length.

11. The method of claim 10 wherein the machining is an abrasive machining.

12. The method of claim 1 being a modification of a baseline process for machining a baseline slot and wherein the selecting at least one parameter shifts a surface mismatch location when compared with the baseline slot while maintaining compatibility with a blade root of a corresponding baseline blade.

13. The method of claim 12 wherein the selecting at least one parameter shifts the surface mismatch when compared with the baseline slot without adding a machining pass.

14. A method for cutting a blade root retention slot in a turbine engine disk element, the method comprising:
 forming a precursor slot in the element, the precursor slot having first and second sidewalls and a base;
 subsequent to said forming, machining a convoluted profile into the first and second sidewalls; and
 subsequent to said machining, passing a rotating abrasive bit through the precursor slot to machine said base, the abrasive bit rotating about an axis off-normal to a direction of said passing,
wherein the method further comprises:
 modeling a cutting performance of the rotating abrasive bit incorporating a chip trapping intensity parameter and a heat intensity parameter;
 calculating the heat intensity parameter including calculation of a product of thermal diffusivity of material of the precursor and a contact length; and
 selecting at least one parameter of the abrasive bit and its passing so as to avoid tool loading where removed chips/swarf stick onto the bit.

15. The method of claim 14 wherein method includes calculating the chip trapping intensity parameter as a product of a specific removal rate and the contact length.

16. The method of claim 14 wherein said machining broadens and deepens the base.

17. The method of claim 14 wherein the forming comprises machining with a grinding wheel rotating about a wheel axis essentially perpendicular to a direction of passing said grinding wheel and essentially circumferential to a central longitudinal axis of the disk element.

18. The method of claim 14 wherein the machining comprises machining with a profiling hit having a convoluted longitudinal profile complementary to said convoluted profile of said slot sidewalls.

19. The method of claim 14 wherein the passing smoothes transitions between said first and second sidewalls and said base.

20. The method of claim 14 wherein during the passing, the bit axis essentially lies along a radial plane of the element at an angle of between 60° and 85° relative to said direction of said passing.

21. The method of claim 14 wherein the passing increases an outward concavity of the base.

* * * * *